United States Patent
Kuchimaru

(10) Patent No.: US 11,092,797 B2
(45) Date of Patent: Aug. 17, 2021

(54) ENDOSCOPIC IMAGE CAPTURING DEVICE

(71) Applicant: Olympus Corporation, Hachioji (JP)

(72) Inventor: Toru Kuchimaru, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/666,464

(22) Filed: Oct. 29, 2019

(65) Prior Publication Data
US 2020/0064618 A1   Feb. 27, 2020

Related U.S. Application Data

(63) Continuation of application No. PCT/JP2018/007565, filed on Feb. 28, 2018.

(30) Foreign Application Priority Data

May 1, 2017 (JP) .............................. JP2017-091220

(51) Int. Cl.
*G02B 23/24* (2006.01)
*H04N 5/225* (2006.01)
(Continued)

(52) U.S. Cl.
CPC ........ *G02B 23/243* (2013.01); *A61B 1/00193* (2013.01); *A61B 1/05* (2013.01);
(Continued)

(58) Field of Classification Search
CPC ... A61B 1/00096; A61B 1/00193; A61B 1/05; G02B 23/2415; G02B 23/243;
(Continued)

(56) References Cited

U.S. PATENT DOCUMENTS

| 4,926,257 A | 5/1990 | Miyazaki |
| 2008/0151041 A1* | 6/2008 | Shafer ................ A61B 1/00009 348/45 |

(Continued)

FOREIGN PATENT DOCUMENTS

| JP | S63-155115 A | 6/1988 |
| JP | H08-015616 A | 1/1996 |

(Continued)

OTHER PUBLICATIONS

International Search Report together with the Written Opinion from related International Application No. PCT/JP2018/007565 dated May 22, 2018.

*Primary Examiner* — Joon Kwon
(74) *Attorney, Agent, or Firm* — Scully, Scott, Murphy & Presser, P.C.

(57) ABSTRACT

The disclosed technology is directed to an endoscopic image capturing device. The image capturing device comprises a first objective lens frame a first lens compartment housing therein first optical members of a first objective optical system and a second lens compartment housing therein second optical members of a second objective optical system that is positioned contiguously with the first objective optical system. A second objective lens frame is disposed for sliding movement with respect to the first objective lens frame in optical axis directions. An image capturing frame is disposed for sliding movement with respect to the second objective lens frame in the optical axis directions and housing therein an image capturing device that has an image capturing surface onto which first and second optical images that has passed through the first and second objective optical systems are focused. A positioning member is disposed in the objective optical system hole.

6 Claims, 5 Drawing Sheets

(51) Int. Cl.
    *G02B 7/02*         (2021.01)
    *A61B 1/00*         (2006.01)
    *A61B 1/05*         (2006.01)
    *H04N 13/218*    (2018.01)
    *H04N 13/204*    (2018.01)

(52) U.S. Cl.
    CPC ......... *G02B 7/021* (2013.01); *G02B 23/2484* (2013.01); *H04N 5/2254* (2013.01); *H04N 13/218* (2018.05); *H04N 13/204* (2018.05); *H04N 2005/2255* (2013.01)

(58) Field of Classification Search
    CPC .... G02B 23/2484; G02B 7/021; G03B 35/18; H04N 13/204; H04N 13/218; H04N 2005/2255; H04N 5/2254; H04N 5/22541; H04N 5/2258
    See application file for complete search history.

(56) References Cited

U.S. PATENT DOCUMENTS

| | | |
|---|---|---|
| 2012/0212813 A1 | 8/2012 | Breidenthal et al. |
| 2012/0220828 A1* | 8/2012 | Iwasaki ................ A61B 1/0058 600/109 |
| 2014/0357951 A1 | 12/2014 | Muller et al. |
| 2016/0106303 A1* | 4/2016 | Birnkrant ................ A61B 1/051 600/109 |
| 2016/0259159 A1* | 9/2016 | Matsui ................ H04N 13/239 |
| 2017/0139198 A1* | 5/2017 | Kibayashi .......... A61B 1/00045 |
| 2017/0273540 A1* | 9/2017 | Yoshinaga ................ A61B 1/00 |

FOREIGN PATENT DOCUMENTS

| | | |
|---|---|---|
| JP | H09-122068 A | 5/1997 |
| JP | H09-127435 A | 5/1997 |
| JP | H10-174673 A | 6/1998 |
| JP | 2001-221961 A | 8/2001 |
| JP | 2003-005313 A | 1/2003 |
| JP | 2004-298431 A | 10/2004 |
| JP | 4533735 B2 | 9/2010 |
| JP | 4745632 B2 | 8/2011 |
| JP | 2014-510579 A | 5/2014 |
| JP | 2014-230788 A | 12/2014 |
| JP | 2015-126288 A | 7/2015 |
| JP | 5897222 B2 | 3/2016 |

* cited by examiner

ENDOSCOPIC IMAGE CAPTURING DEVICE

CROSS-REFERENCE TO RELATED APPLICATIONS

This application is a continuation application of PCT Application No. PCT/JP2018/007565 filed on Feb. 28, 2018, which in turn claim priority to the Japanese Patent Application No. 2017-91220 filed on May 1, 2017 in Japan which is hereby incorporated by reference in its entirety.

TECHNICAL FIELD

The technology disclosed herein generally relates to an endoscopic image capturing device including a lens frame with two objective optical systems juxtaposed therein.

DESCRIPTION OF THE RELATED ART

In recent years, endoscopes have been used in the medical and industrial fields. Some endoscopes are known as electronic endoscopes having a solid-state image capturing device such as a charged coupled device (CCD) disposed in the distal-end portion of an insertion portion. An electronic endoscope displays an optical image focused onto an image capturing surface of a CCD on the screen of a display device for observation.

Japanese Patent Laid-open No. Hei 09-127435 discloses a stereoscopic endoscopic image capturing device including two focusing optical systems which is small in size, easy to handle, and capable of obtaining good images. In the stereoscopic endoscopic image capturing device, the two focusing optical systems have their peripheral edge portions partially cut off to make themselves D-shaped, thereby reducing a space in which the focusing optical systems is placed and making the stereoscopic endoscopic image capturing device smaller in size. In addition, the two focusing optical systems are separated from each other by a light shield plate, and further, a restriction means is included, preventing left and right images from interfering with each other and bringing out a restriction effect to produce good images that that are free of ghosts, flares, etc.

In the stereoscopic endoscopic image capturing device described hereinbefore, a lens frame that holds part of the focusing optical systems is divided into upper and lower lens frames that are individually movable in optical axis directions. After the upper and lower lens frames have made focus adjustments for the respective optical systems, they can be fixed in position.

However, in the stereoscopic endoscopic image capturing device described hereinbefore, the divided lens frames, each holding the focusing optical system, are individually moved in the optical axis directions for making focus adjustments while the light shield plate is being placed to separate the focusing optical systems from each other. Therefore, when the lens frames are moved in the optical axis directions, there are risks such as the light shield plate being deformed or the lens frames being prevented from smoothly moving by the light shield plate, making it difficult to make highly accurate focus adjustments.

BRIEF SUMMARY OF EMBODIMENTS

Accordingly, one aspect of the disclosed technology is directed to an endoscopic image capturing device. The image capturing device comprises a first objective lens frame having an objective optical system hole defined therein that includes a first lens compartment housing therein first optical members of a first objective optical system and a second lens compartment housing therein second optical members of a second objective optical system that is positioned contiguously with the first objective optical system. A second objective lens frame is disposed for sliding movement with respect to the first objective lens frame in optical axis directions and housing therein part of the second optical members of the second objective optical system. An image capturing frame is disposed for sliding movement with respect to the second objective lens frame in the optical axis directions and housing therein an image capturing device that has an image capturing surface onto which a first optical image that has passed through the first objective optical system and a second optical image that has passed through the second objective optical system are focused. A positioning member is disposed in the objective optical system hole defined in the first objective lens frame for placing in predetermined positions the first optical members of the first objective optical system disposed in the first lens compartment and the second optical members of the second objective optical system disposed in the second lens compartment.

The objective optical system hole has the first lens compartment, the second lens compartment, and a joint portion defined by a positioning space housing the positioning member therein and interconnecting the first lens compartment and the second lens compartment into the objective optical system hole. The positioning member is a rectangular plate member having a predetermined thickness or a cylindrical rod member having a predetermined diametrical dimension disposed between the first objective optical system and the second objective optical system. The plate member includes a resilient portion pressing the first objective optical system and the second objective optical system in directions away from each other. The rod member includes a tapered face pressing the first objective optical system and the second objective optical system in directions away from each other.

Another aspect of the disclosed technology is directed to an endoscopic image capturing device. The image capturing device comprises a first objective lens frame, a second objective lens frame, an image capturing frame, and a distal-end lens frame all of which being attached to one another to define a frame of the endoscopic image capturing device. The first objective lens frame includes a first lens compartment housing containing first optical members of a first objective optical system and a second lens compartment housing containing second optical members of a second objective optical system that are positioned contiguously with the first objective optical system. The second objective lens frame is positioned for sliding movement with respect to the first objective lens frame in optical axis directions and housing therein part of the second optical members of the second objective optical system. An image capturing device is configured to be positioned in the image capturing frame such that the image capturing frame positioned for sliding movement with respect to the second objective lens frame in the optical axis directions. The image capturing device includes an image capturing surface onto which respective first and second optical images are focused with one another by passing through respective first and second objective optical systems. A positioning member is disposed in the first objective optical system for placing the first optical members in predetermined positions of the first objective optical system and the second optical members in predetermined positions of the second objective optical system so as to set an optical axis distance between contiguous respective first and second objective optical systems while preventing adjacent respective first and second optical members from contacting one another.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

In one aspect of the disclosed technology, there is provided an endoscopic image capturing device including a first objective lens frame having an objective optical system hole defined therein that includes a first lens compartment housing therein optical members of a first objective optical system and a second lens compartment housing therein optical members of a second objective optical system that is disposed in juxtaposed relation to the first objective optical system, a second objective lens frame disposed for sliding movement with respect to the first objective lens frame in optical axis directions and housing therein part of the optical members of the second objective optical system, an image capturing frame disposed for sliding movement with respect to the second objective lens frame in the optical axis directions and housing therein an image capturing device that has an image capturing surface onto which an optical image that has passed through the first objective optical system and an optical image that has passed through the second objective optical system are focused, and a positioning member disposed in the objective optical system hole defined in the first objective lens frame, for placing in predetermined positions the optical members of the first objective optical system disposed in the first lens compartment and the optical members of the second objective optical system disposed in the second lens compartment.

It is an object of the disclosed technology to provide an endoscopic image capturing device that is able to set an optical axis distance between juxtaposed objective optical systems to a high precision while preventing adjacent lenses of the juxtaposed objective optical systems from contacting one another and from being positioned off-center, and is also able to make focus adjustments easily and highly accurately.

Embodiments of the disclosed technology will hereinafter be described with reference to the drawings.

In each of the figures used in the description that follows, some of the components are drawn to different scales in order to illustrate themselves in sizes large enough to be recognized in the figures. In other words, the disclosed technology should not be limited to the numbers, shapes, size proportions, and relative positional relationships of the components depicted in the figures.

Figure 1:
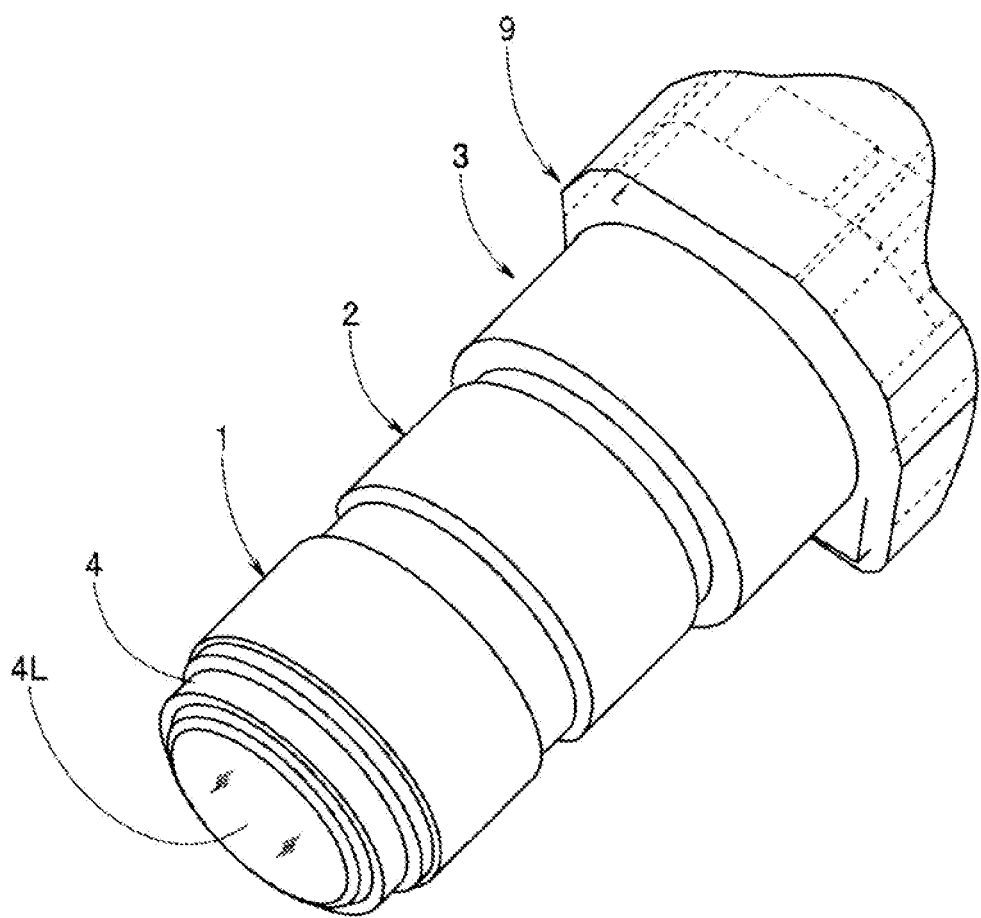
FIG. 1 is a view illustrative of an endoscopic image capturing device.

An endoscopic image capturing device illustrated in FIG. 1 is a stereoscopic endoscopic image capturing device 9 and mainly includes a first objective lens frame 1, a second objective lens frame 2, an image capturing frame 3, and a distal-end lens frame 4. The distal-end lens frame 4 provides a distal end of the stereoscopic endoscopic image capturing device 9, and has a distal-end lens 4L.

Figure 2:
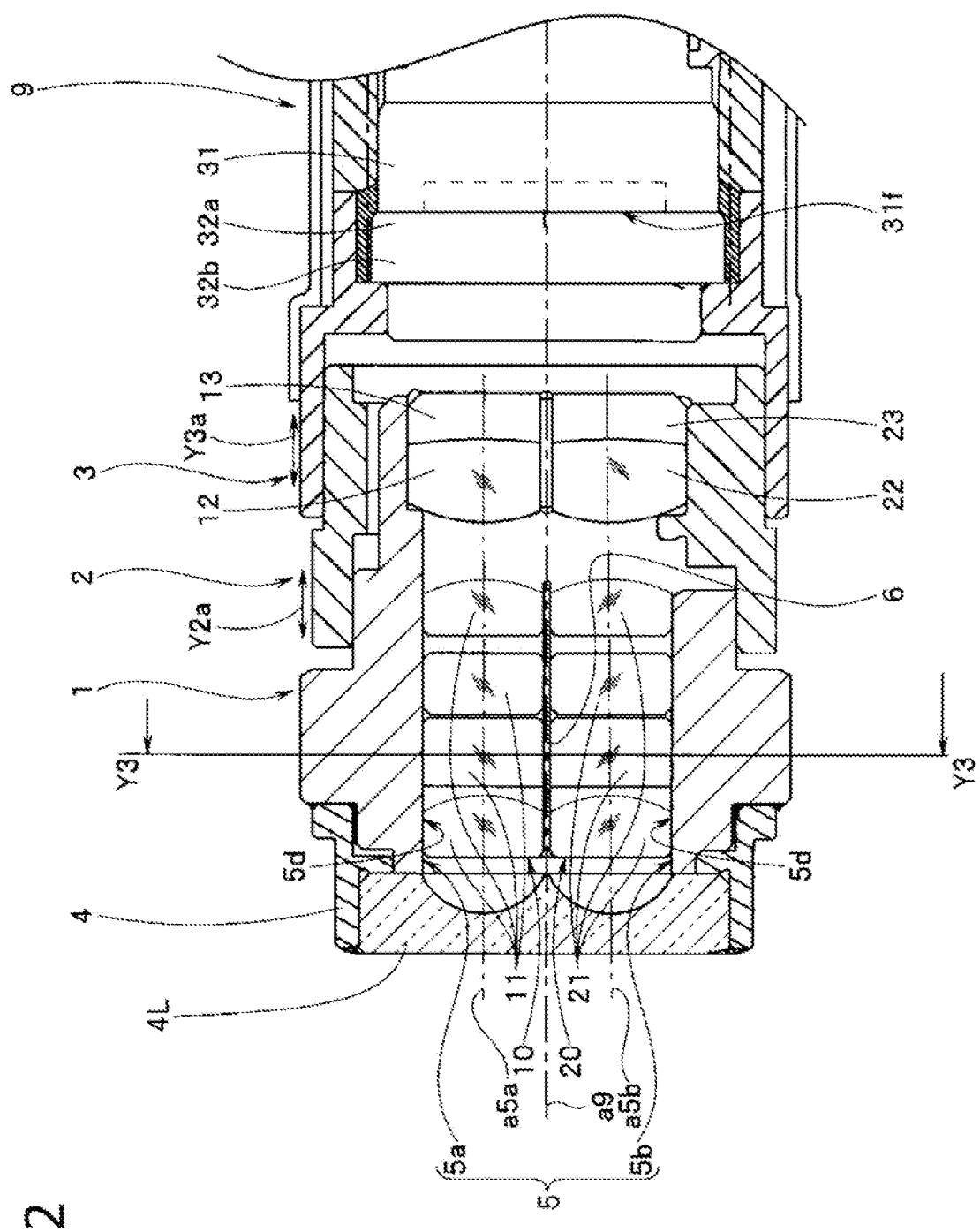
FIG. 2 is a longitudinal cross-sectional view illustrative of the endoscopic image capturing device.

As illustrated in FIG. 2, the second objective lens frame 2 is disposed for sliding movement in optical axis directions with respect to the first objective lens frame 1 as indicated by arrows Y2a. The image capturing frame 3 is disposed for sliding movement in the optical axis directions with respect to the second objective lens frame 2 as indicated by arrows Y3a.

To the image capturing frame 3, there are attached an image capturing device 31, cover lenses 32a and 32b, and the like. A plurality of optical lenses 22 and 23 as part of second optical members of a second objective optical system 20 are disposed in the second objective lens frame 2. A first objective optical system 10 and the second objective optical system 20 are disposed in the first objective lens frame 1.

The first objective optical system 10 includes a plurality of optical lenses 11, 12, and 13 as first optical members. The second objective optical system 20 includes a plurality of optical lenses 21 as second optical members that are other than the plurality of optical lenses 22 and 23.

The optical members of the first objective optical system 10 and the optical members of the second objective optical system 20 are identical members. Therefore, the plurality of optical lenses 11 and optical lenses 12 and 13 of the first objective optical system 10 and the plurality of optical lenses 21 and optical lenses 22 and 23 of the second objective optical system 20 are substantially similar optical lenses.

An optical image that has passed through the first objective optical system 10 and an optical image that has passed through the second objective optical system 20 are focused onto an image capturing surface 31f of the image capturing device 31.

Figure 3:
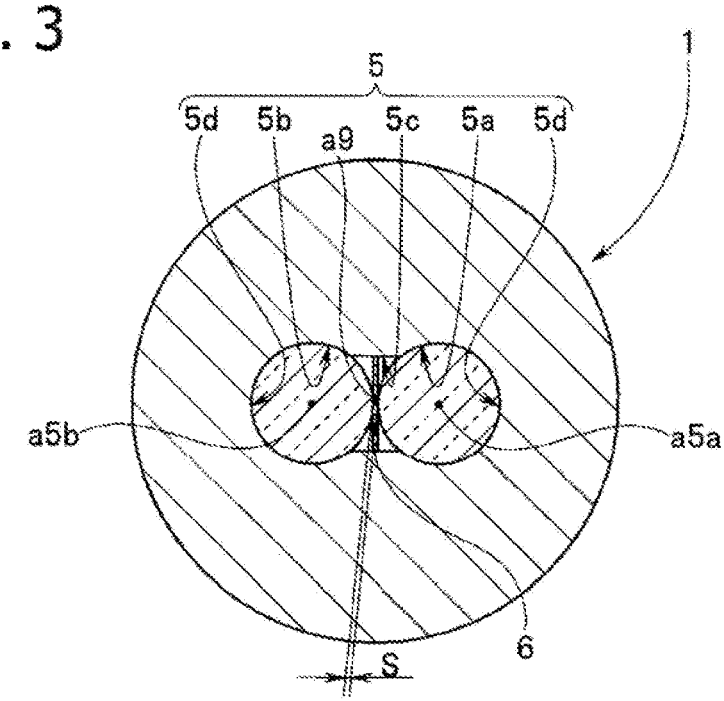
FIG. 3 is a cross-sectional view taken along line Y3-Y3 of FIG. 2, illustrating objective optical system holes and a positioning member disposed in the objective optical system holes.

As illustrated in FIGS. 2 and 3, the first objective optical system 1 has a through hole 5 defined therein along a longitudinal axis a9. The through hole 5 is an objective optical system hole and is in a shape of dumbbells. The through hole 5 thus has a first housing hole 5a and a second housing hole 5b that are of a substantially circular shape and are disposed in juxtaposed relation to each other, and a junction hole 5c. The junction hole 5c is a joint portion that interconnects the first housing hole 5a and the second housing hole 5b into one through hole 5.

The first housing hole 5a is a first lens compartment that houses therein the plurality of optical lenses 11, 12, and 13 of the first objective optical system 10. The second housing hole 5b is a second lens compartment that houses therein the plurality of optical lenses 21 of the second objective optical system 20. The junction hole 5c is a positioning space in which a spacer 6 as a positioning member is housed.

The spacer 6 is a hard member formed as a rectangular plate member. The spacer 6 has a predetermined thickness. The spacer 6 doubles as a light shield member or an antireflection member.

The numeral references 5d represent holding surfaces. The holding surfaces 5d are disposed respectively in the first housing hole 5a and the second housing hole 5b. Specifically, the first holding surfaces 5d are an inner peripheral hole surface positioned opposite the junction hole 5c across an axis a5a of the first housing hole 5a and an inner peripheral hole surface positioned opposite the junction hole 5c across an axis a5b of the second housing hole 5b.

With the first objective lens frame 1 thus constructed, a worker places the plurality of optical lenses 11, 12, and 13 in the first housing hole 5a and places the plurality of optical lenses 21 in the second housing hole 5b.

With the lenses thus housed, the worker places the spacer 6 in a clearance S between the optical lenses 11 and the optical lenses 21 that are disposed adjacent to each other in the junction hole 5c.

Now, the plurality of optical lenses 11, 12, and 13 housed in the first housing hole 5a are shifted toward the holding surface 5d of the first housing hole 5a by the spacer 6. On the other hand, the plurality of optical lenses 21 housed in the second housing hole 5b are shifted toward the holding surface 5d of the second housing hole 5b by the spacer 6.

Then, an adhesive (not illustrated) is applied between an inner peripheral surface of the first objective lens frame 1 and outer peripheral surfaces of the optical lenses 11 and 21 that are positioned in a foremost end of the first objective lens frame 1, thereby securing the optical lenses 11 and 21 to the first objective lens frame 1. The first objective lens frame 1 with the two objective optical systems 10 and 20 disposed therein is thus completed.

As a result, the spacer 6 is able to reliably prevent the optical members including the optical lenses of the objective optical systems from contacting each other. Furthermore, the spacer 6 shifts the optical members disposed in the adjacent housing holes 5a and 5b toward the holding surfaces 5d and positions them in predetermined positions, making a distance between an optical axis of the first objective optical system 10 and an optical axis of the second objective optical system 20 highly accurate and also reducing fitting backlash to restrain the optical members from being positioned off-center. As the spacer 6 is disposed in the clearance S, the adhesive applied between the first objective lens frame 1 and the outer peripheral surfaces of the optical lenses 11 is prevented from flowing rearwardly through the clearance S and from being deposited within effective diameters of the optical lenses 11 and 21 that are positioned in subsequent stages.

These functions of the spacer 6 make it possible to dispose the first objective optical system 10 and the second objective optical system 20 highly accurately in juxtaposed relation in the first objective lens frame 1 for improved optical characteristics.

In addition, the spacer 6 disposed in the clearance S is able to eliminate such problems that the optical members disposed in adjacent holes would otherwise contact each other and that light rays having passed through one of the objective optical systems would otherwise enter the other objective optical system.

The spacer 6 is not limited to a hard member and may be made of a variable-volume material such as silicone or rubber.

The first objective lens frame 1 with the two objective optical system 10 and 20 disposed therein, the second objective lens frame 2 with the optical lenses 22 and 23 of the second objective optical system 20 disposed therein, and the image capturing frame 3 with the image capturing device 31, etc. disposed therein, that are constructed as described hereinbefore, are assembled together into the stereoscopic endoscopic image capturing device 9 by the worker.

On this occasion, the first objective lens frame 1, the second objective lens frame 2, and the image capturing frame 3 are mounted respectively on a first jig, a second jig, and a third jig, not illustrated, and focus adjustments are made by the worker. At this time, the first objective lens frame 1 is mounted on the first jig, the second objective lens frame 2 is mounted on the second jig, and the image capturing frame 3 is mounted on the third jig.

With the frames mounted on the respective jigs, the worker first makes focus adjustments such that an optical image that has passed through the first objective optical system 10 is focused onto the image capturing surface 31f of the image capturing device 31. On this occasion, the worker makes positional adjustments to secure the second jig in position and move the first jig in the optical axis directions, to move the third jig in the optical axis directions or to move the first jig and the third jig in the optical axis directions, thereby making focus adjustments.

Then, the worker makes focus adjustments such that an optical image that has passed through the second objective optical system 20 is focused onto the image capturing surface 31f of the image capturing device 31. On this occasion, the worker makes positional adjustments to secure the first jig and the third jig in the positions used in the adjustment described hereinbefore and move the second jig in the optical axis directions, thereby making focus adjustments.

As a result, the focus adjustments for focusing an optical image that has passed through the first objective optical system 10 onto the image capturing surface 31f of the image capturing device 31 and the focus adjustments for focusing an optical image that has passed through the second objective optical system 20 onto the image capturing surface 31f of the image capturing device 31 can be made by making the positional adjustments for moving the frames 1, 2, and 3 in the optical axis directions.

By thus placing the spacer 6 in the clearance S between the optical lenses 11 and the optical lenses 21 that are disposed adjacent to each other in the junction hole 5c, there is obtained the first objective lens frame 1 in which the distance between the optical axis of the first objective optical system 10 disposed in the first housing hole 5a and the optical axis of the second objective optical system 20 disposed in the second housing hole 5b is made highly accurate and fitting backlash of the plurality of optical members disposed in the first housing hole 5a and fitting backlash of the plurality of optical members disposed in the second housing hole 5b are reduced. Then, the first objective lens frame 1, the second objective lens frame 2 with the optical lenses 22 and 23 of the second objective optical system 20 disposed therein, and the image capturing frame 3 with the image capturing device 31, etc. disposed therein are assembled together, and the frames 1, 2, 3 are moved in the optical axis directions to adjust focus, thereby producing the stereoscopic endoscopic image capturing device 9.

As a consequence, the stereoscopic endoscopic image capturing device 9 that has achieved desired optical performance is obtained.

In the embodiment described hereinbefore, the spacer 6 as the positioning member is illustrated as a rectangular plate member. However, the positioning member is not limited to the spacer 6 and may be plate members with resilient portions as illustrated in FIGS. 4A through 4C or may be rod members as illustrated in FIGS. 5A through 5C.

Modifications of the positioning member will hereinafter be described by way of example with reference to FIGS. 4A through 4C.

Figure 4A:
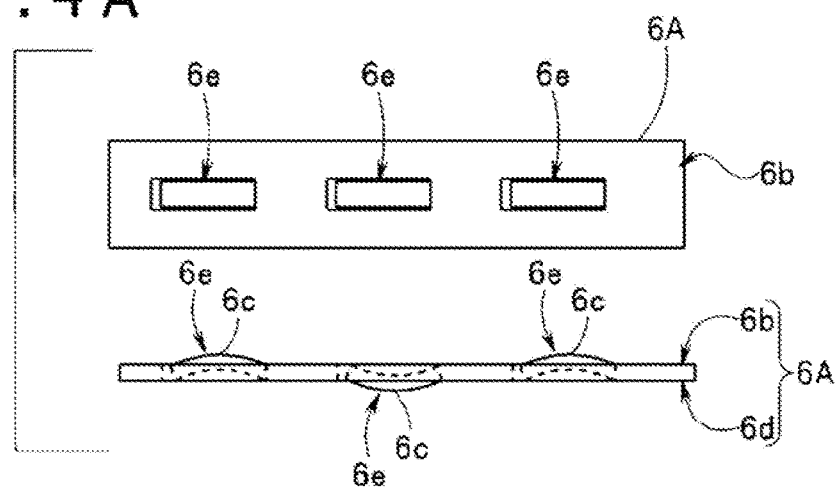
FIG. 4A is a view illustrative of a spacer having resilient portions according to a modification of the positioning member.
Figure 4B:
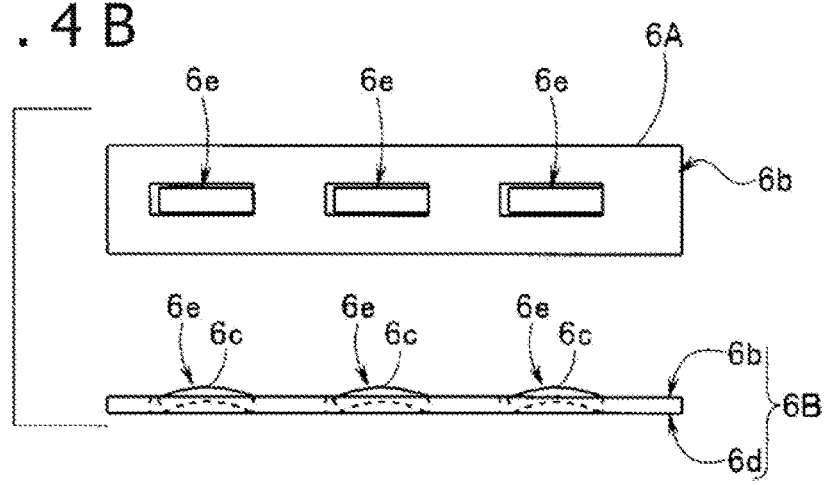
FIG. 4B is a view illustrative of a modification of the spacer having the resilient portions.
Figure 4C:
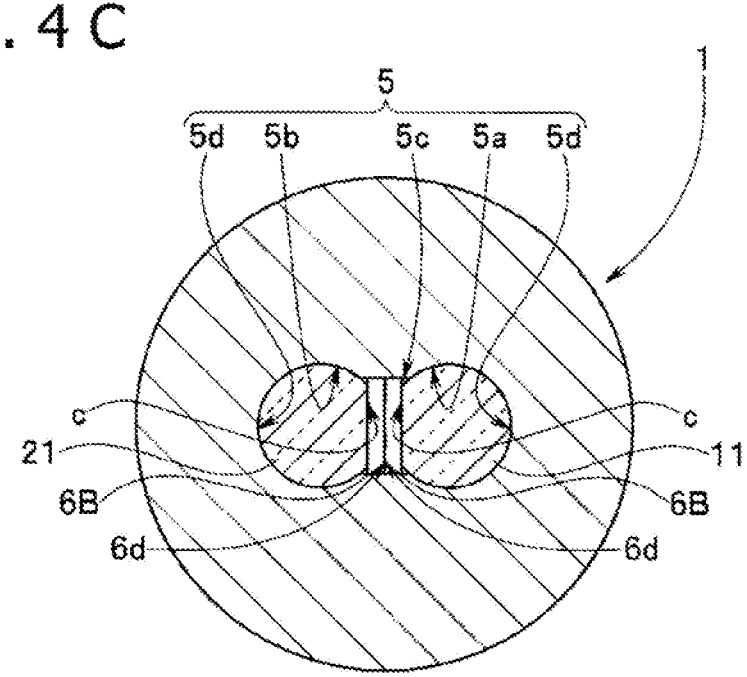
FIG. 4C is a view depicting spacers illustrated in FIG. 4B that are disposed in a superposed fashion in a junction hole.
Figure 5A:
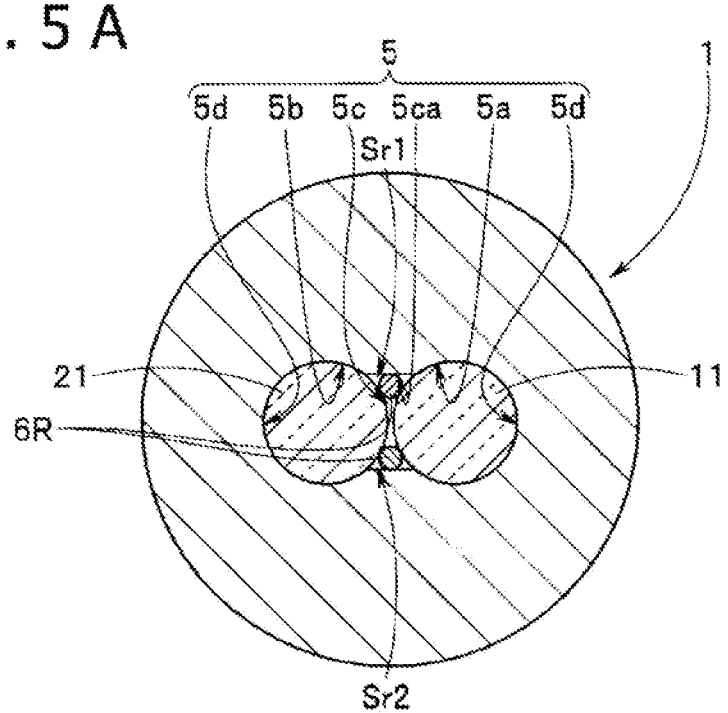
FIG. 5A is a view illustrative of rod members disposed in a junction hole according to a modification of the positioning member.
Figure 5B:
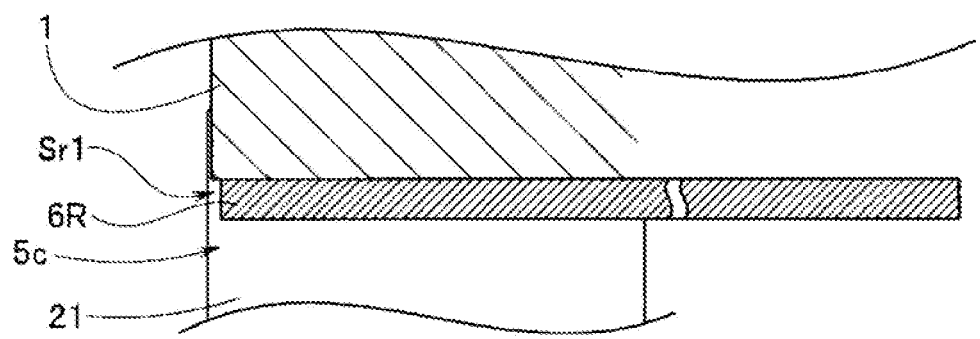
FIG. 5B is a view illustrative of a shape of one of the rod members.
Figure 5C:
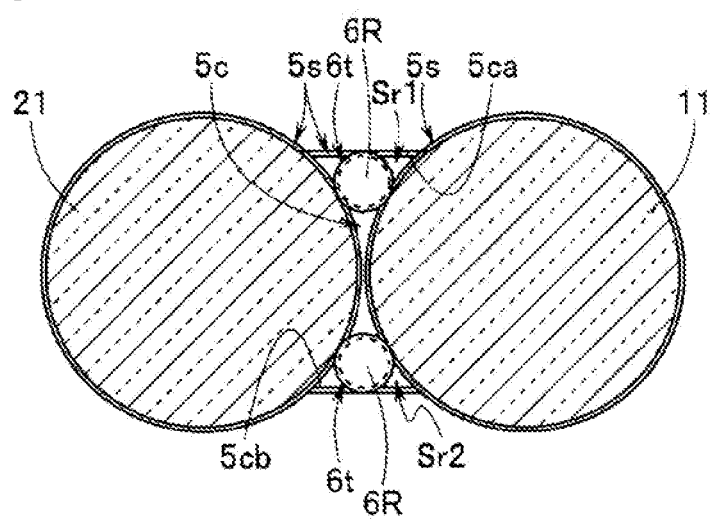
FIG. 5C is a view illustrative of a manner in which rod members having tapered faces operate.

A positioning member illustrated in FIG. 4A is a spacer 6A having resilient portions 6e. The spacer 6A has a thickness that is the same as the thickness of the spacer 6. The spacer 6A has the resilient portions 6e for abutting against predetermines ones of the plurality of optical lenses 11 and 21.

The resilient portions 6e are formed by bending a hard plate member. The resilient portions 6e include two abutment faces 6c protruding from one surface 6b of the spacer 6A and one abutment face 6c protruding from another surface 6d of the spacer 6A.

As with the spacer 6, the spacer 6A is placed in the clearance S between the optical lenses 11 and the optical lenses 21 that are disposed adjacent to each other in the junction hole 5c. When the spacer 6A is placed into the junction hole 5c, the abutment faces 6c are brought into contact with the optical lenses 11 and 21 and elastically deformed into a plate shape.

With the spacer 6A disposed in the clearance S, some of the plurality of optical lenses 11 disposed in the first housing hole 5a and some of the plurality of optical lenses 11 disposed in the second housing hole 5b are normally pressed in directions away from each other under the resilient forces from the resilient portions 6e. In other words, the pressed lenses are pressed against the holding surfaces 5d that are positioned in the respective opposite directions.

With this arrangement, some of the plurality of optical lenses 11 and 21 disposed in the housing holes 5a and 5b are pressed against the holding surfaces 5d under the resilient force from the resilient portions 6e of the spacer 6A. As a result, fitting backlash is reduced to restrain more effectively the optical members from being positioned off-center.

As illustrated in FIG. 4B, in a case where the optical lenses 11 and 21 and the like have cut surfaces c to make themselves D-shaped, thereby reducing the size of the lenses, two spacers 6B may be placed in the junction hole 5c, as illustrated in FIG. 4C.

Each of the spacers 6B illustrated in FIG. 4C has a plurality of (three in FIG. 4C) resilient portions 6e. There are as many resilient portions 6e as the number of the optical lenses 11 and 12. The resilient portions 6e of the spacer 6B are disposed respectively on the cut surfaces c of the lenses 11 and 12.

The resilient portions 6e of the present embodiment are also formed by bending a hard plate member. However, in the present embodiment, all abutment faces 6c protrude from one surface 6b, whereas another surface 6d is a flat surface. The other surface 6d functions as a mating surface. The two spacers 6B are disposed in the junction hole 5c with their other surfaces 6d mating with each other.

With this arrangement, the plurality of optical lenses 11 and 21 disposed in the housing holes 5a and 5b are pressed in directions away from each other under the resilient forces from the resilient portions 6e of the spacers 6B to move in the directions of the holding surfaces 5d.

As a result, the optical lenses 11, 21 disposed respectively in the adjacent housing holes 5a, 5b are normally pressed in the directions of the holding surfaces 5d under the resilient forces from the resilient portions 6e of the spacers 6B, making the distance between the optical axes highly accurate and greatly reducing fitting backlash to restrain more effectively the optical members from being positioned off-center.

Consequently, the first objective optical system 10 and the second objective optical system 20 are disposed highly accurately in juxtaposed relation in the first objective lens frame 1 for improved optical characteristics.

Modifications of the positioning member will hereinafter be described by way of example with reference to FIGS. 5A through 5C.

Positioning members illustrated in FIG. 5A are rod members 6R each having a predetermined diametrical dimension. The rod members 6R are disposed in a first rod space Sr1 defined by a side 5ca of the junction hole 5c and outer peripheral surfaces of the lenses 11 and 21 and a second rod space Sr2 defined by a side 5cb of the junction hole 5c and outer peripheral surfaces of the lenses 11 and 21. In other words, two rod members 6R are disposed respectively in the first rod space Sr1 and the second rod space Sr2. As illustrated in FIG. 5B, each of the rod members 6R is of a straight shape.

According to the present embodiment, since one of the rod members 6R is disposed in the first rod space Sr1 and the other in second rod space Sr2, the plurality of lenses 11 and 21 disposed in the housing holes 5a and 5b are shifted toward the holding surfaces 5d by the two rod members 6R.

As a result, the distance between the optical axes of the first objective optical system 10 and the second objective optical system 20 is made highly accurate, and fitting backlash is reduced to restrain the optical members from being positioned off-center. The first objective optical system 10 and the second objective optical system 20 are disposed highly accurately in juxtaposed relation in the first objective lens frame 1 for improved optical characteristics.

The rod members 6R are made of a hard material or a variable-volume material. As illustrated in FIG. 5C, the outer peripheral surface of the optical lens 11, the outer peripheral surface of the optical lens 12, and the sides 5ca, 5cb of the junction hole 5c, which jointly define the rod spaces Sr1, Sr2, have slanted surfaces 5s that are inclined at a predetermined angle, and the rod members 6R have tapered faces 6t at ends thereof that are inclined at the angle of the slanted surfaces.

With this arrangement, when one of the rod members 6R is placed in the first rod space Sr1 or the other rod member 6R is placed in the second rod space Sr2, the tapered face 6t is pressed against the slanted surfaces 5s, defining positions where the rods are disposed. When the tapered faces 6t are held and pressed against the slanted surfaces 5s, the tapered faces 6t press the optical lenses 11 and 21 in directions away from each other.

These functions of the rod members 6R make it possible to dispose the first objective optical system 10 and the second objective optical system 20 highly accurately in juxtaposed relation in the first objective lens frame 1 for improved optical characteristics. Moreover, as the worker is able to judge when the rod members 6R are placed in a predetermined state in the rod spaces Sr1, Sr2 by feeling that the rod members have been pressed against the lenses, working efficiency is improved.

The disclosed technology is not limited to only the embodiments described hereinbefore and various changes and modifications may be made without departing from the scope of the invention.

In sum, one aspect of the disclosed technology is directed to an endoscopic image capturing device. The image capturing device comprises a first objective lens frame having an objective optical system hole defined therein that includes a first lens compartment housing therein first optical members of a first objective optical system and a second lens compartment housing therein second optical members of a second objective optical system that is positioned contiguously with the first objective optical system. A second objective lens frame is disposed for sliding movement with respect to the first objective lens frame in optical axis directions and housing therein part of the second optical members of the second objective optical system. An image capturing frame is disposed for sliding movement with respect to the second objective lens frame in the optical axis directions and housing therein an image capturing device that has an image capturing surface onto which a first optical image that has passed through the first objective optical system and a second optical image that has passed through the second objective optical system are focused. A positioning member is disposed in the objective optical system hole defined in the first objective lens frame for placing in predetermined positions the first optical members of the first objective optical system disposed in the first lens compartment and the second optical members of the second objective optical system disposed in the second lens compartment.

The objective optical system hole has the first lens compartment, the second lens compartment, and a joint portion defined by a positioning space housing the positioning member therein and interconnecting the first lens compartment and the second lens compartment into the objective optical system hole. The positioning member is a rectangular plate member having a predetermined thickness or a cylindrical rod member having a predetermined diametrical dimension disposed between the first objective optical system and the second objective optical system. The plate member includes a resilient portion pressing the first objective optical system and the second objective optical system in directions away from each other. The rod member includes a tapered face pressing the first objective optical system and the second objective optical system in directions away from each other.

Another aspect of the disclosed technology is directed to an endoscopic image capturing device. The image capturing device comprises a first objective lens frame, a second objective lens frame, an image capturing frame, and a distal-end lens frame all of which being attached to one another to define a frame of the endoscopic image capturing device. The first objective lens frame includes a first lens compartment housing containing first optical members of a first objective optical system and a second lens compartment housing containing second optical members of a second objective optical system that are positioned contiguously with the first objective optical system. The second objective lens frame is positioned for sliding movement with respect to the first objective lens frame in optical axis directions and housing therein part of the second optical members of the second objective optical system. An image capturing device is configured to be positioned in the image capturing frame such that the image capturing frame positioned for sliding movement with respect to the second objective lens frame in the optical axis directions. The image capturing device includes an image capturing surface onto which respective first and second optical images are focused with one another by passing through respective first and second objective optical systems. A positioning member is disposed in the first objective optical system for placing the first optical members in predetermined positions of the first objective optical system and the second optical members in predetermined positions of the second objective optical system so as to set an optical axis distance between contiguous respective first and second objective optical systems while preventing adjacent respective first and second optical members from contacting one another.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

This application is based upon and claims the benefit of priority of the Japanese Patent Application No. 2017-91220, filed on May 1, 2017, the entire contents of which are incorporated herein by reference.

What is claimed is:

1. An endoscopic image capturing device comprising:
   a first objective optical system comprising first optical members;
   a second objective optical system comprising second optical members;
   a first objective lens frame defining an objective optical system hole, the objective optical system hole having a first lens compartment for housing the first optical members of the first objective optical system in the first lens compartment, the objective optical system hole further having a second lens compartment for housing the second optical members of the second objective optical system in the second lens compartment, the second objective optical system being positioned contiguously with the first objective optical system;
   a second objective lens frame disposed for sliding movement with respect to the first objective lens frame in optical axis directions, the second objective lens frame housing a part of the second optical members of the second objective optical system;
   an image capturing frame disposed for sliding movement with respect to the second objective lens frame in the optical axis directions, the image capturing frame housing an image capturing device that has an image capturing surface onto which a first optical image that has passed through the first objective optical system and a second optical image that has passed through the second objective optical system are focused;
   a positioning member disposed in the objective optical system hole for placing in predetermined positions the first optical members of the first objective optical system disposed in the first lens compartment and the second optical members of the second objective optical system disposed in the second lens compartment, and
   a distal lens disposed distally relative to the first objective lens frame;
   wherein the first lens compartment includes all of the first optical members of the first objective optical system, and
   the second lens compartment includes the second optical members of the second objective optical system other than the part of the second optical members.

2. The endoscope image capturing device of claim 1, wherein the objective optical system hole has the first lens compartment, the second lens compartment, and a joint portion defined by a positioning space housing the positioning member therein, the joint portion interconnecting the first lens compartment and the second lens compartment into the objective optical system hole.

3. The endoscope image capturing device of claim 1, wherein the positioning member is a rectangular plate member having a predetermined thickness or a cylindrical rod member having a predetermined diametrical dimension disposed between the first objective optical system and the second objective optical system.

4. The endoscope image capturing device of claim 3, wherein the plate member includes a resilient portion pressing the first objective optical system and the second objective optical system in directions away from each other.

5. The endoscope image capturing device of claim 3, wherein the rod member includes a tapered face pressing the first objective optical system and the second objective optical system in directions away from each other.

6. An endoscopic image capturing device comprising:
   a first objective optical system comprising first optical members;
   a second objective optical system comprising second optical members;
   a first objective lens frame, a second objective lens frame, an image capturing frame, and a distal-end lens frame all of which being attached to one another to define a frame of the endoscopic image capturing device, the first objective lens frame includes a first lens compartment containing the first optical members of the first objective optical system and a second lens compartment containing the second optical members of the second objective optical system, the second objective optical system being positioned contiguously with the first objective optical system,
   the second objective lens frame is positioned for sliding movement with respect to the first objective lens frame in optical axis directions the second objective lens frame housing a part of the second optical members of the second objective optical system,
   an image capturing device configured to be positioned in the image capturing frame such that the image capturing frame is positioned for sliding movement with respect to the second objective lens frame in the optical axis directions, the image capturing device includes an image capturing surface onto which respective first and second optical images being focused with one another by passing through the first and second objective optical systems, respectively;
   a positioning member disposed in the first objective optical system for placing the first optical members in predetermined positions of the first objective optical system and the second optical members in predetermined positions of the second objective optical system so as to set an optical axis distance between contiguous respective first and second objective optical systems while preventing adjacent respective first and second optical members from contacting one another; and
   a distal lens housed in the distal-end lens frame, the distal-end lens frame being disposed distally relative to the first objective lens frame;
   wherein the first lens compartment includes all of the first optical members of the first objective optical system, and
   the second lens compartment includes the second optical members of the second objective optical system other than the part of the second optical members.

* * * * *